United States Patent [19]

Holt, Jr.

[11] 4,286,949
[45] Sep. 1, 1981

[54] PORTABLE DENTAL APPARATUS

[76] Inventor: Raleigh A. Holt, Jr., 122 Pinehill Rd. NW., Orangeburg, S.C. 29115

[21] Appl. No.: 121,823

[22] Filed: Feb. 15, 1980

[51] Int. Cl.³ .............................................. B05B 9/04
[52] U.S. Cl. ..................................... 433/103; 433/77; 433/101
[58] Field of Search .................. 433/116, 77; 239/332, 239/333

[56] References Cited

U.S. PATENT DOCUMENTS

| 2,629,539 | 2/1953 | Drewes | 239/333 |
|---|---|---|---|
| 3,077,665 | 2/1963 | Saltzman | 433/103 |
| 3,081,542 | 3/1963 | Sherfey | 433/101 |
| 3,553,840 | 1/1971 | Bordelon | 633/77 |

Primary Examiner—Robert Peshock
Attorney, Agent, or Firm—B. P. Fishburne, Jr.

[57] ABSTRACT

A compact portable and essentially unitized dental apparatus having a stable support base and a top carrying handle enables the visiting dentist to perform all necessary dental services at nursing homes, homes of invalids, hospital emergency rooms and in the field as with military or missionary personnel. A compressor-compressor motor unit forms the body on which other components of the apparatus are mounted. Electrical or gasoline engine compressor operation is feasible. The apparatus will operate high and low speed dental drills, a three-way syringe, and high volume suction device. Individual components are standard commerical items.

2 Claims, 3 Drawing Figures

PORTABLE DENTAL APPARATUS

BACKGROUND OF THE INVENTION

An unfulfilled need exists in the prior art for a truly portable dental machine for use by dentists who are "on call" to nursing homes, homes of invalids, hospital emergency rooms and the like. While the prior patented art contains some teachings of partly mobile dental units, none of these units approaches the compactness, overall reduced weight, and comparative low cost of manufacturing of the present invention. No known prior art device possesses the ability of the present invention to be bodily lifted, carried and to be placed in the most convenient operating position on any level support surface by means of a simple lifting handle and a stable supporting base, each attached to the motor-compressor unit which forms the body of the apparatus.

Some examples of the known prior art are shown in the following United States patents:
U.S. Pat. No. 2,351,943
U.S. Pat. No. 3,427,719
U.S. Pat. No. 3,949,480.

The portable dental apparatus can be enclosed and operated in a noise suppression box or enclosure, not shown, to further enhance its utility. It may also be equipped with conventional quick disconnect couplings on dental and vacuum units so that these components can be quickly transferred to another compressor by the dentist. This feature will allow the dentist to purchase only the dental and vacuum units for connection to a compressor at the hospital or nursing home. If preferred, the dentist can purchase the completely self-contained apparatus including the motorized compressor so as to be independent of outside equipment.

Other features and advantages of the invention will become apparent during the course of the following detailed description.

DETAILED DESCRIPTION

Figure 1:
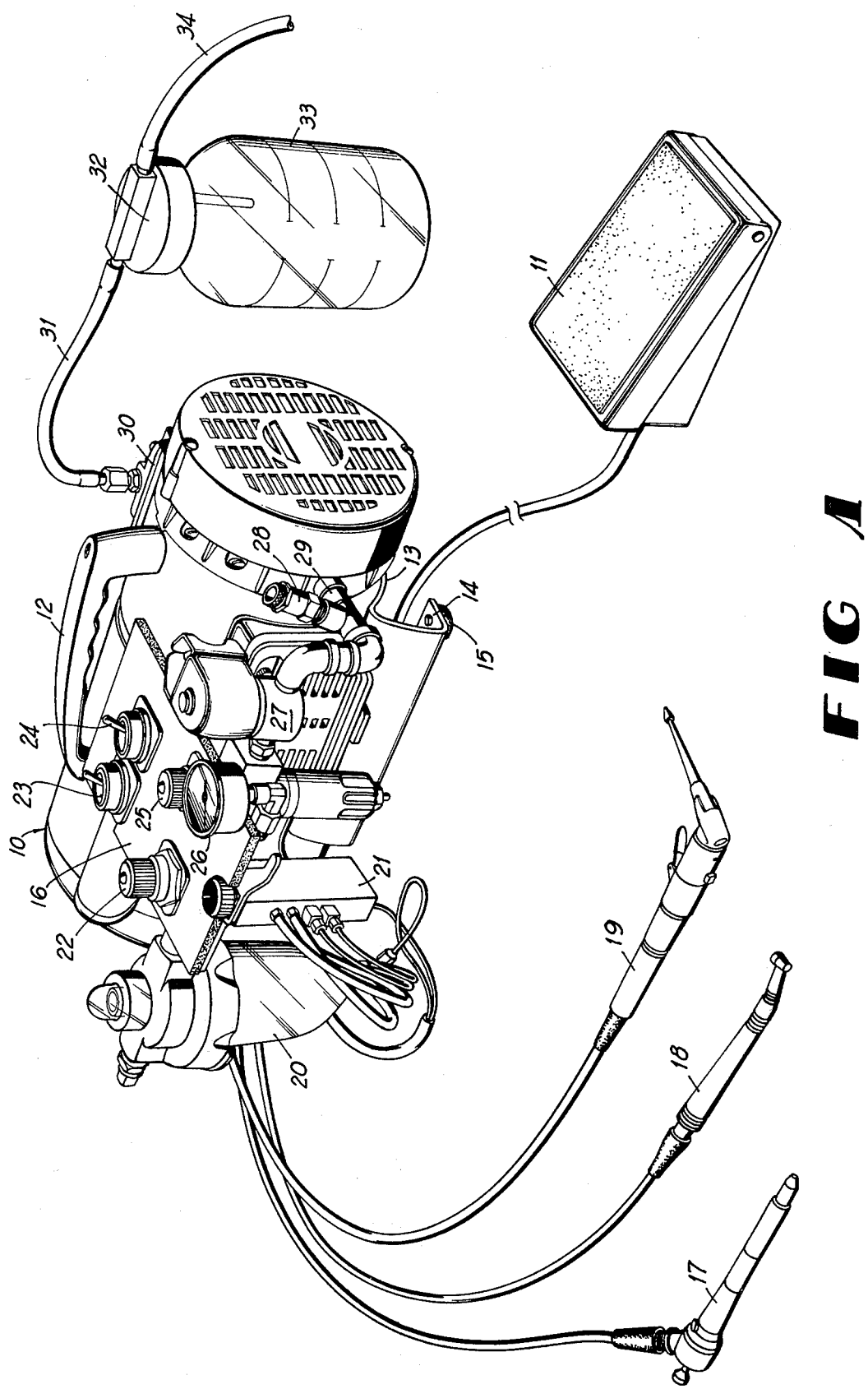
FIG. 1 is a perspective view of a portable dental apparatus in accordance with the invention.
Figure 2:
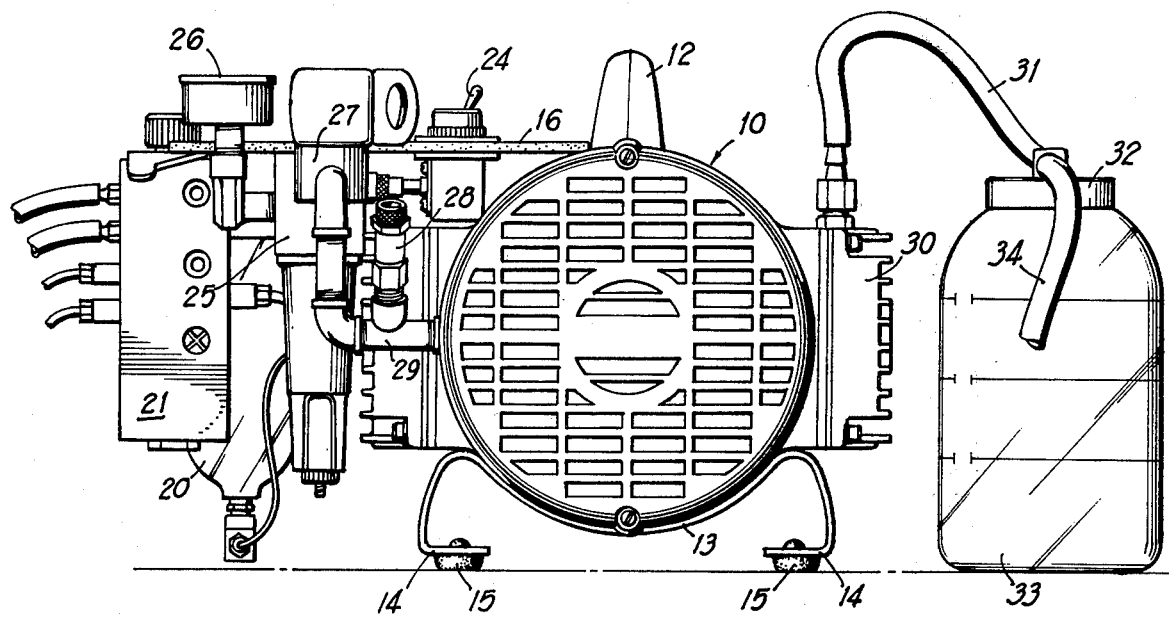
FIG. 2 is an end elevational view of the apparatus.
Figure 3:
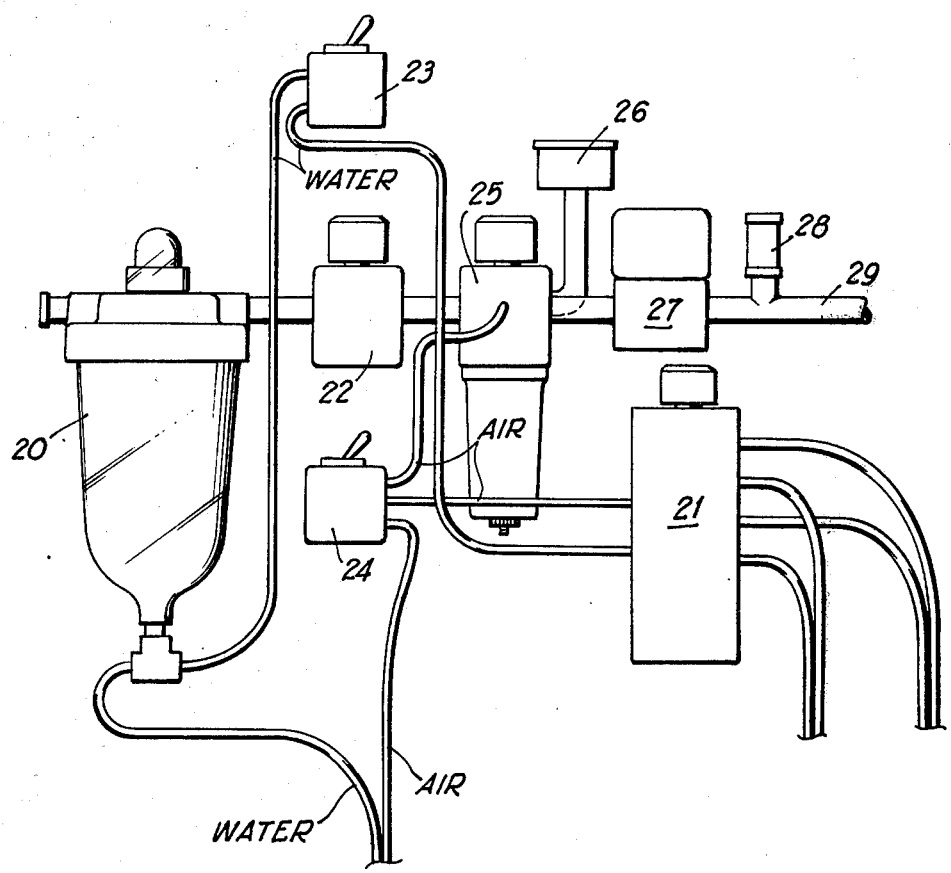
FIG. 3 is a partly schematic elevational view of interconnected components of the apparatus.

Referring to the drawings in detail, wherein like numerals designate like parts, a self-contained portable dental apparatus comprises an elongated cylindrical motor compressor unit 10 including a conventional compressor and associated electrical drive motor. The compressor-motor is controlled by an electrical foot pedal control 11 of a type well-known in the art and widely used on dental machines and therefore requiring no detailed description.

Atop the unit 10 which forms the body portion of the apparatus and rigid therewith is a single sturdy carrying handle 12 by means of which the dentist can conveniently lift, transport and position the apparatus as required for most efficient usage.

The cylindrical motor-compressor unit 10 is cradled on a supporting arcuate base plate 13 having opposite side parallel longitudinal level support flanges 14, preferably equipped with rubber-like feet 15. The support flanges 14 extend along a major portion of the length of the unit 10 for the sake of stability. The arrangement enables the positioning of the portable apparatus on any convenient generally level support surface, such as a table, floor surface or the like.

Attached to the motor-compressor unit 10 with the assistance of a level support panel 16 are a number of per se conventional operating components found on any dental machine, stationary, semi-portable or otherwise. As these various components are conventional and coact and operate in the same manner on this portable apparatus as in any other dental machine, only a brief description of them is required. More particularly, the operating components include a slow speed conventional drill or hand piece 17, a high speed hand piece 18, and a three-way dental syringe 19 capable of delivering air, water, and a mixture of air and water, as required. The usual water container 20 is secured to the supporting panel 16 and a conventional hand piece selector 21 is mounted on the panel 16 at the outer edge thereof to enable selective use of the required dental hand piece.

A metering valve 22 for water pressure is mounted near the container 20 and a water on-off switch 23 is placed next to an air on-off switch 24, both in ready reach of the dentist. The use of the panel 16 places all of the components and their operational controls upright at the top of the apparatus for maximum convenience when the apparatus is resting on a level support surface.

An air pressure metering valve 25 is placed next to water pressure valve 22 and an adjacent air pressure gage 26 with upwardly facing dial is also arranged as shown.

The assembly further comprises a solenoid controlled valve 27 connected to the compressor-motor to relieve pressure in the system when the compressor-motor is turned off. A safety relief valve 28 is also connected in the main air line 29 leading from the compressor of the unit 10. Operating air pressure for all components is delivered by the compressor through this line or conduit 29.

The portable apparatus additionally comprises a vacuum cylinder 30 fixed to the side of the cylindrical unit 10 away from the panel 16 and parts thereon. This helps to distribute weight and balance the apparatus. The vacuum cylinder 30 is connected by a flexible hose 31 to a conventional vacuum assembly 32 including a container 33 with a hose extension 34 leading to the patient.

With the portable apparatus transported and positioned in a convenient location on a level support surface, the dentist proceeds to work on the patient in the usual manner at a nursing home, home of an invalid or the like. A noise suppression box for the apparatus, not shown, can be provided and this is an optional feature. The use of quick disconnect couplings at strategic points allow the dental and vacuum components to be readily transferred from one motor-compressor unit to another. This is another optional feature. As illustrated in the drawings, the apparatus is self-contained, essentially unitary and has no dependence on outside equipment except an electrical outlet in the case of an electrical drive motor for the compressor. A small internal combustion engine can be used to power the compressor for field operation as with the military or missionaries in the field.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. A portable dental treatment apparatus comprising a unitized body portion in the form of a horizontal axis motor-compressor unit, a carrying handle fixed on the top of said unit, a supporting base for the apparatus fixed on the bottom of said unit including wide stance feet adjacent to the opposite sides of said unit for the support of the apparatus on a horizontal support surface, a treatment component support and control panel fixed on said unit near the top of the unit in a horizontal plane spaced above and parallel to a plane in which said feet are located, a plurality of conventional dental treatment components bodily mounted on and supported by said panel and being operatively connected with the compressor of said motor-compressor unit, said panel and said treatment components on the panel being disposed adjacent to one side of said unit in cantilevered relationship to the unit, and a vacuum cylinder unit fixed on the other side of said motor-compressor unit in counterbalancing relationship to said platform and the treatment components thereon and adapted for connection to a conventional dental vacuum assembly.

2. A portable dental treatment apparatus as defined in claim 1, and a main air supply line for the apparatus connected between the compressor of said motor-compressor unit and said treatment components and having pressure relief valve means connected therein, and a treadle control device for the motor of said motor-compressor unit operatively coupled therewith.

* * * * *